(12) United States Patent
Steffee et al.

(10) Patent No.: US 6,348,071 B1
(45) Date of Patent: *Feb. 19, 2002

(54) SPINAL DISC

(75) Inventors: Arthur D. Steffee, Cleveland, OH (US); E. Raymond S. Ross, Manchester (GB); Robert D. Fraser, Adelaide (AU); Gary L. Lowery, Gainesville, FL (US)

(73) Assignee: DePuy AcroMed, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/183,105

(22) Filed: Oct. 30, 1998

Related U.S. Application Data

(63) Continuation of application No. 08/962,578, filed on Oct. 31, 1997, now Pat. No. 6,139,579.

(51) Int. Cl.[7] ................................................ A61F 2/44
(52) U.S. Cl. .................................. 623/17.15; 623/17.16
(58) Field of Search ........................... 623/17.11–17.16

(56) References Cited

U.S. PATENT DOCUMENTS

| | | |
|---|---|---|
| 4,714,469 A | 12/1987 | Kenna |
| 4,911,718 A | 3/1990 | Lee et al. |
| 4,917,704 A | 4/1990 | Frey et al. |
| 4,932,969 A | 6/1990 | Frey et al. |
| 4,997,432 A | 3/1991 | Keller |
| 5,071,437 A | 12/1991 | Steffee |
| 5,258,043 A | 11/1993 | Stone |
| 5,306,308 A | 4/1994 | Gross |
| 5,306,309 A | 4/1994 | Wagner et al. |
| 5,370,697 A | 12/1994 | Baumgartner |
| 5,397,364 A | 3/1995 | Kozak et al. |
| 5,458,643 A | 10/1995 | Oka et al. |
| 5,480,444 A | 1/1996 | Incavo et al. |
| 5,514,180 A | 5/1996 | Heggeness et al. |
| 5,522,899 A | 6/1996 | Michelson |
| 5,534,029 A | 7/1996 | Shima |
| 5,534,030 A | 7/1996 | Navarro et al. |
| 5,545,229 A | 8/1996 | Parsons et al. |
| 5,556,431 A | 9/1996 | Büttner-Janz |
| 5,683,464 A | 11/1997 | Wagner |
| 5,702,450 A | 12/1997 | Bisserie |
| 5,716,415 A | 2/1998 | Steffee |

FOREIGN PATENT DOCUMENTS

| | | |
|---|---|---|
| DE | 0 538 183 A1 | 7/1992 |
| EP | 0 599 419 A2 | 11/1993 |
| EP | 610837 | 8/1994 |
| WO | WO 91/05521 | 5/1991 |
| WO | WO 94/12123 | 6/1994 |
| WO | 00082 | 1/1995 |

OTHER PUBLICATIONS

*Treatise on Adhesion And Adhesives*, Vol. 7, edited by J. Dean Minford (1991), pp. 280–281.

McKenzie, Alvin H. *Fernstrom Intervertebral Disc Arthroplasty: A long Term Evaluation*, Orthopaedics International Edition Jul./Aug. 1995, vol. 3 No. 4, pp. 313–324.

Hawkins, Monica Vuno, Ph.D. *The Design and Evaluation of a Thermoplastic Elastomeric (TPE) Lumbar Intervertebral Disc Spacer*, Order No. 9213914 UMI 300 N. Zeeb Rd. Ann Arbor, MI 48106, (1991) pp. 62–71, 124–127, and 168–171.

*Primary Examiner*—Michael J. Milano
(74) *Attorney, Agent, or Firm*—Maginot, Addison & Moore

(57) ABSTRACT

A spinal disc prosthesis to replace a damaged spinal disc in a spinal column (16) of a human, includes a body (10) having an upper surface (52) engageable with the upper vertebra (12) and a lower surface (152) engageable with the lower vertebra (14). The body (10) includes a crescent-shaped projection (62, 162) extending from one of the upper and lower surfaces (52, 152) of the body for receipt in a cavity in the adjacent vertebra (12, 14).

19 Claims, 4 Drawing Sheets

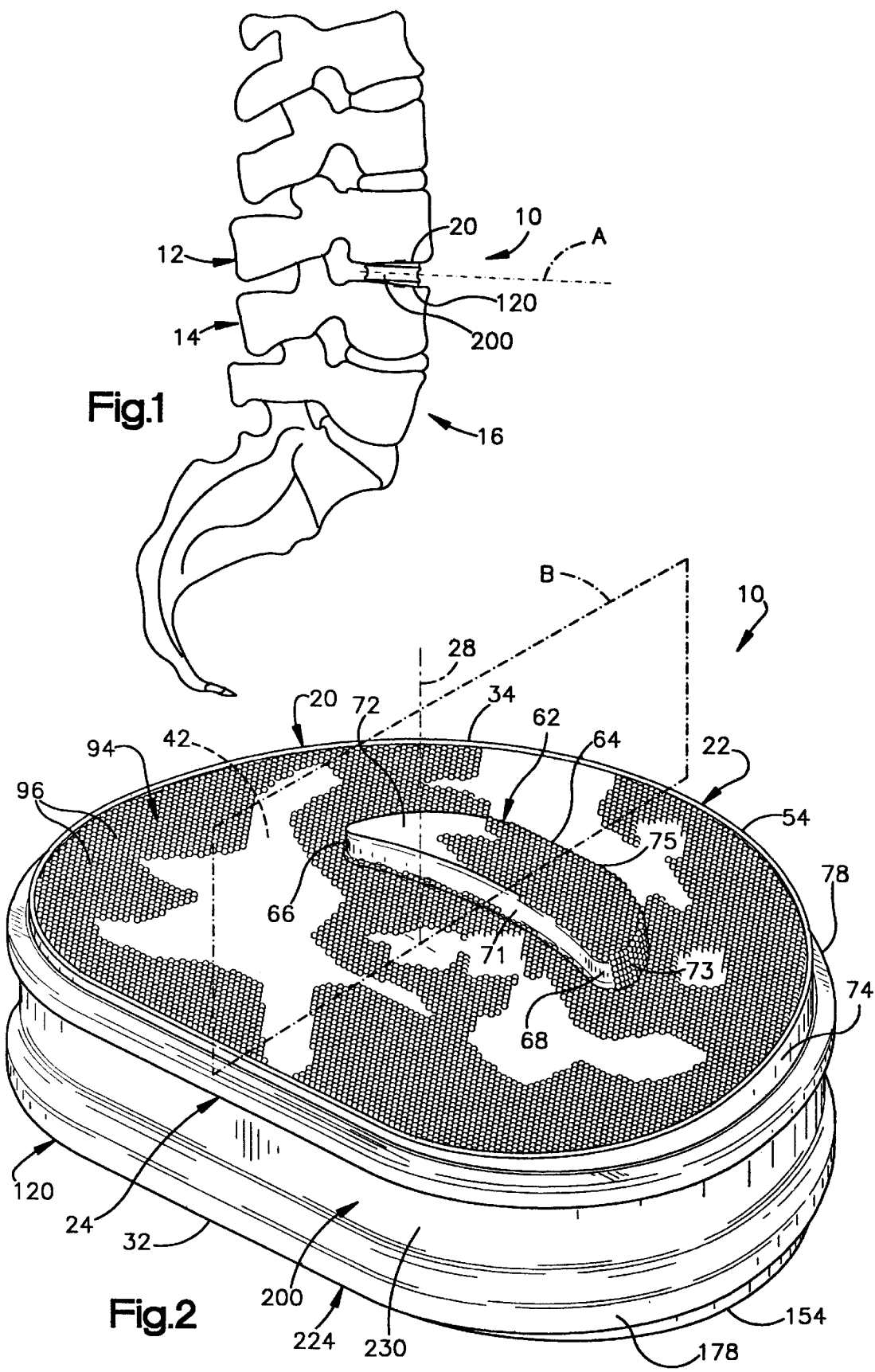

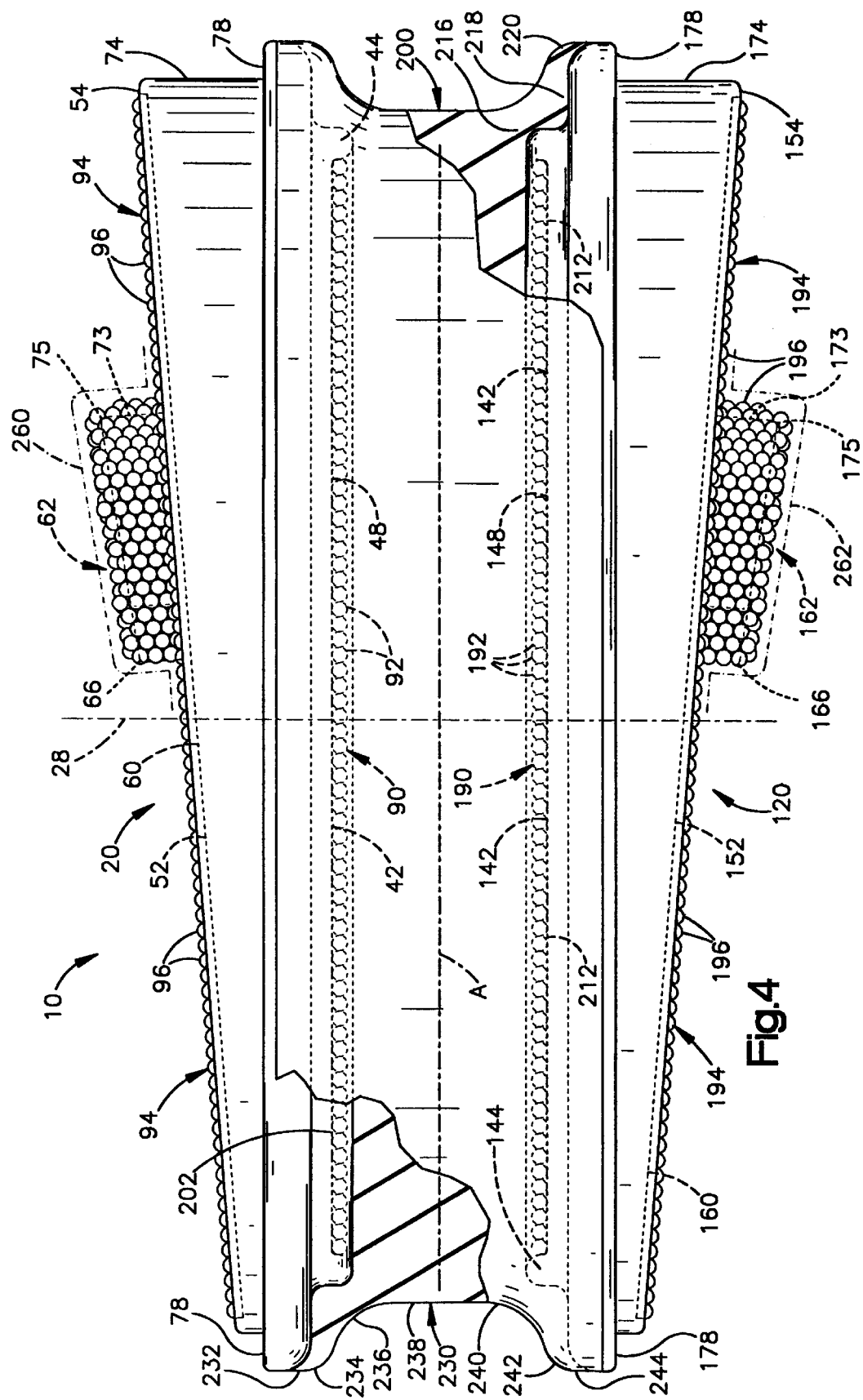

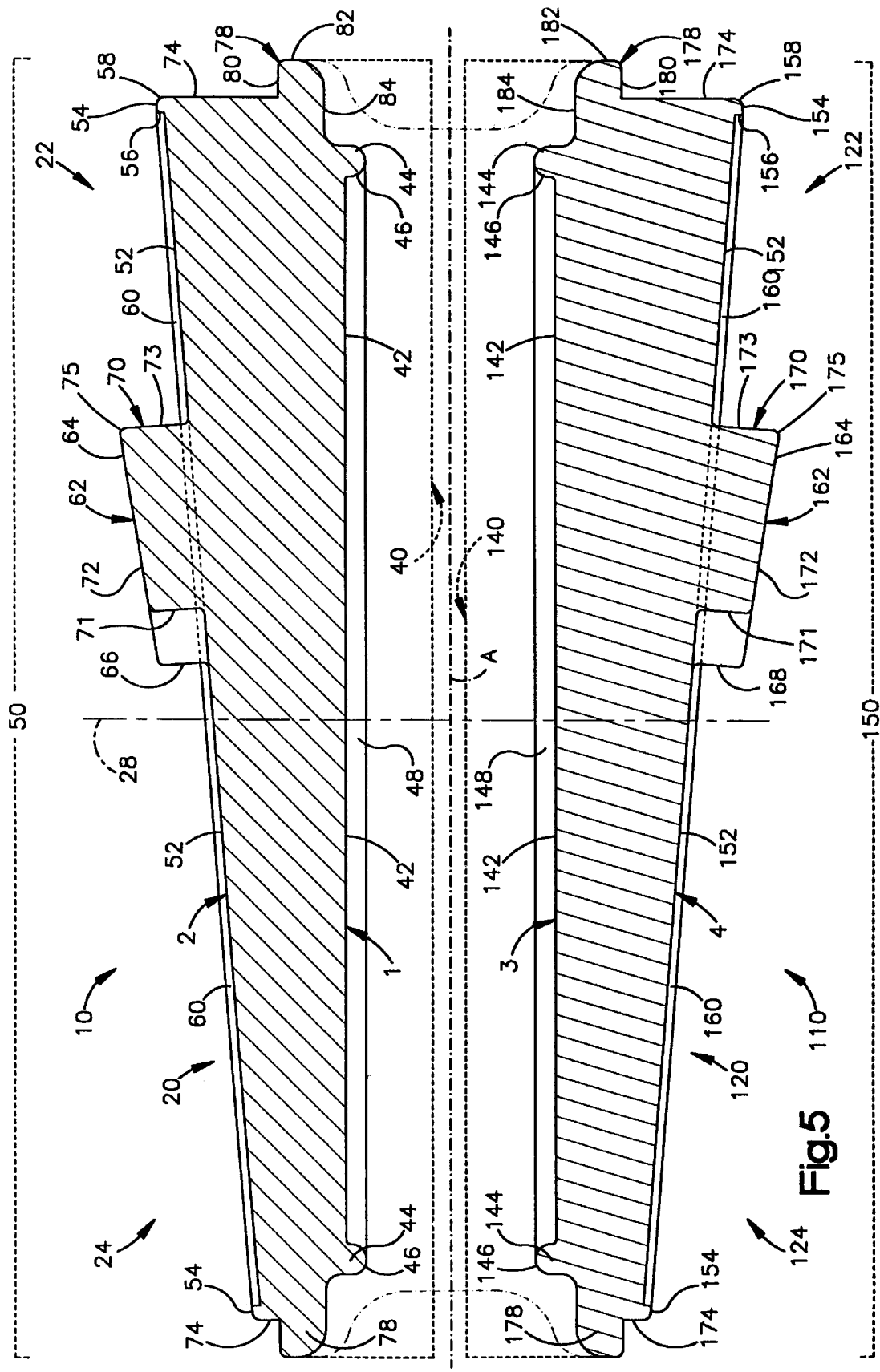

SPINAL DISC

This application is a continuation of co-pending Application Ser. No. 08/962,578, filed on Oct. 31, 1997 now U.S. Pat. No. 6,139,579.

BACKGROUND AND SUMMARY OF THE INVENTION

The present invention relates to a spinal disc prosthesis to replace a damaged or degenerated spinal disc in a spinal column of a human.

U.S. Pat. Nos. 5,017,437 and 5,534,030 disclose typical spinal disc prostheses to replace a damaged or degenerated spinal disc in a spinal column of a human. The discs disclosed in these patents include a pair of rigid plates adhered to opposite surfaces of a body of elastomeric material.

The disc when in use is positioned between adjacent vertebrae. The disc is subject to forces which act in the spine including compression forces due to loads on the spine, tension forces due to bending of the spine, and torsional forces due to twisting of the spine. These forces can be applied simultaneously to the disc. These forces tend to cause relative motion between the disc and the adjacent vertebrae.

The discs disclosed in these patents have spaced projections for location in cavities in the adjacent vertebrae. The projections when located in a cavity resist a tendency of the disc to move relative to the vertebrae. Thus, the projections help maintain the disc in position between vertebrae.

The cavities which receive the projections are formed in the vertebrae by the surgeon. The deeper the cavity, the more difficult it is for the surgeon to form the cavity. It is desirable to minimize the depth of the cavity and yet maintain the resistance to relative movement of the disc and vertebrae. In addition, it is desirable for the surgeon to be able to move the disc relative to the vertebrae, at least by a small amount, when the disc is located between the vertebrae. The relatively long, spaced projections of the discs disclosed in U.S. Pat. Nos. 5,017,437 and 5,534,030 require relatively deep cavities and do not readily permit the surgeon to be able to move the disc relative to the vertebrae.

The present invention relates to projections on a spinal disc which projections are received in cavities in the vertebrae between which the disc is located. Each vertebrae has one cavity which receives a respective projection on the disc. The projection and cavity have substantial area contact which minimizes the possibility of the disc being expelled upon relative movement of the vertebrae between which the disc is located. Also, the height of the projection is minimized in order to minimize the depth of the cavity, thus minimizing the amount of distraction of the vertebrae which is necessary when the cavity which is to receive a projection is formed.

Moreover, the spinal discs of the prior art have lobes projecting from the posterior portion of the disc. These lobes have been found to be areas of stress concentration where forces act to separate the rigid plates from the body of elastomeric material. Elimination of these lobes to minimize the stress concentration has been found to be desirable.

BRIEF DESCRIPTION OF THE DRAWINGS

The foregoing and other features of the present invention will become more apparent to one skilled in the art upon reading the following description of a preferred embodiment with reference to the accompanying drawings, wherein:

FIG. 1 is an elevational view of a human spinal column having a spinal disc in accordance with the present invention between adjacent vertebrae of the spinal column;

FIG. 2 is a top perspective view of the spinal disc of FIG. 1;

FIG. 4 is an elevational view, partly in section, of the spinal disc of FIG. 1, taken generally along line 4—4 of FIG. 3;

FIG. 5 is a sectional view of the spinal disc of FIG. 1, taken generally along line 5—5 of FIG. 3 and with parts removed.

DESCRIPTION OF A PREFERRED EMBODIMENT

The present invention relates to an artificial spinal disc prosthesis to replace a damaged or degenerated spinal disc in a spinal column of a human. As representative of the present invention, FIG. 1 illustrates a spinal disc prosthesis, i.e., spinal disc 10. The spinal disc 10 is illustrated in use between adjacent upper and lower vertebrae 12 and 14 of a human spinal column 16. The vertebrae 12 and 14 have portions which face anteriorly (to the right as viewed in FIG. 1) and portions which face posteriorly (to the left as viewed in FIG. 1).

Figure 3:
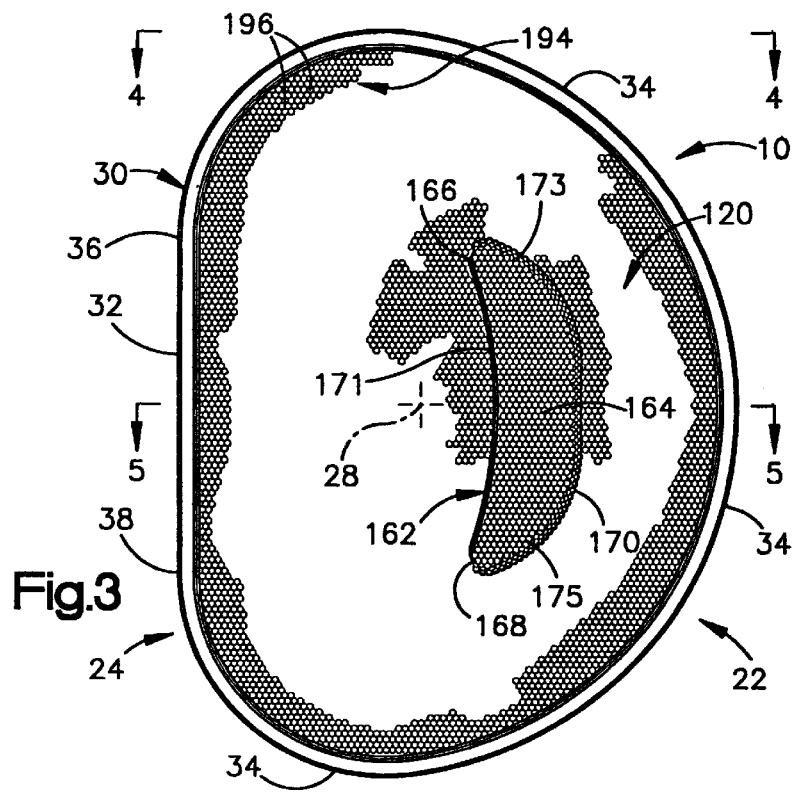
FIG. 3 is a bottom plan view of the spinal disc of FIG. 1.

The disc 10 comprises a first or upper rigid plate 20, a second or lower rigid plate 120, and an elastomeric core 200 interposed between and adhered to the two plates. The upper and lower plates 20 and 120 are identical to each other, and the disc 10 is symmetrical about an anterior-posterior, horizontally extending plane A (FIG. 4) and is also symmetrical about a sagittal plane B (FIG. 3). The terms "upper" and "lower" are used herein with reference to the orientation of the disc 10 when it is implanted in the human body as illustrated in FIG. 1, to distinguish the two identical plates for reference purposes.

The upper plate 20 (FIG. 5) is rigid and is preferably made of a biocompatible metal such as a titanium-vanadium-aluminum alloy having about 90% by weight titanium, about 6% by weight aluminum and about 4% by weight vanadium. Alternatively, the upper plate 20 can be made of any suitable biocompatible material, including but not limited to a composite plastic material. The upper plate 20 is preferably milled out of a single block of metal. The upper plate 20 could, however, be made in a different manner, for example, by casting.

Figure 6:
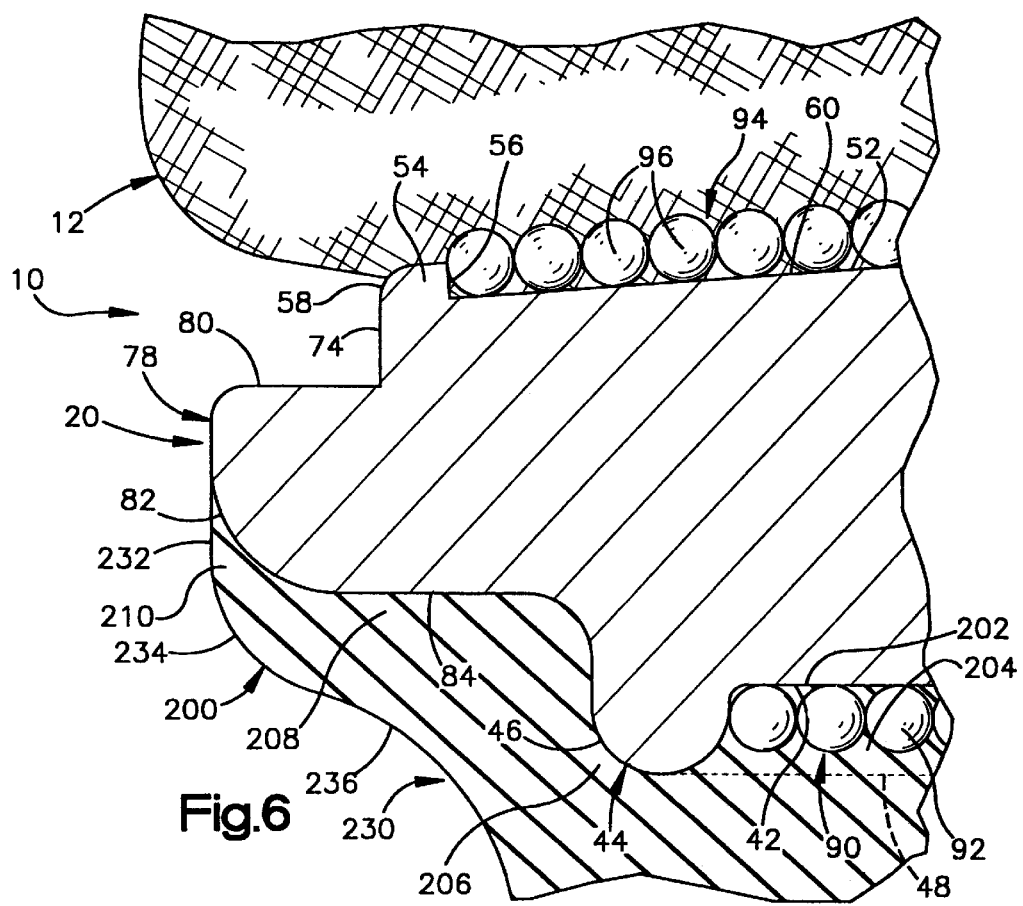
FIG. 6 is an enlarged view of a portion of FIG. 4.

The upper plate 20 has an anterior portion 22 and a posterior portion 24. The anterior portion 22 of the upper plate 20 is that portion of the upper plate which is disposed anteriorly in the spine 16 when the disc 10 is implanted in the spine. The posterior portion 24 of the upper plate 20 is that portion of the upper plate which is disposed posteriorly in the spine 16 when the disc 10 is implanted in the spine. The anterior portion of the upper plate can be said to be located generally on one side (to the right as viewed in FIG. 5) of an axis 28 of the disc 10; the posterior portion of the upper plate can be said to be located generally on the other side (to the left as viewed in FIG. 6) of the axis 28. The axis 28 extends through the disc between the upper and lower plates 20 and 120. The axis 28 extends generally along the length of the spinal column 16 when the disc 10 is implanted in the spinal column.

The configuration of the disc 10 (as viewed in plan) is designed to conform generally to the shape of a natural human spinal disc. The perimeter 30 (FIG. 3) of the disc 10 has a flat posterior portion 32. The perimeter 30 of the disc 10 has a curved convex portion 34 which extends between opposite ends 36 and 38 of the flat portion 32 of the perimeter. The perimeter 30 of the disc 10, including the perimeters of the core 200 and of the plates 20 and 120, does not have any outwardly projecting lobes. The perimeter of the core 200 has the same configuration (as viewed in plan) as the perimeter of the upper and lower plates 20 and 120.

The upper plate 20 has an inner major side surface 40 which is presented downward as viewed in FIG. 5. The inner major side surface 40 includes all of the surface area of the upper plate 20 which is visible from below (in plan) as viewed in FIG. 5. The inner major side surface 40 of the upper plate 20 includes a planar first surface 42 of the upper plate which extends perpendicular to the axis 28. The area of the first surface 42 is at least 65% of the area of the inner major side surface 40 as viewed in plan, that is, with all points on the inner major side surface 40 viewed in a direction parallel to the axis 28. Preferably, the area of the first surface 42 is 75% of the area of the inner major side surface 40.

The first surface 42 is circumscribed by a first rim 44 of the upper plate 20. The first rim 44 has a generally semi-cylindrical cross-sectional configuration as shown in FIG. 5 including an arcuate outer surface 46. The outer surface 46 on the first rim 44, and the first surface 42, together define a shallow cavity or recess 48 in the inner major side surface 40 of the upper plate 20. The first surface 42 forms the bottom of the recess 48. The outer surface 46 on the first rim 44 forms a part of the inner major side surface 40 of the upper plate 20.

The upper plate 20 has an outer major side surface 50 which is presented upward as viewed in FIG. 5. The outer major side surface 50 includes all of the surface area of the upper plate 20 which is visible from above (in plan) as viewed in FIG. 5.

The outer major side surface 50 includes a planar second surface 52 of the upper plate 20. The second surface 52 is circumscribed by a second rim 54 of the upper plate 20. The area of the second surface 52 is greater than the area of the first surface 42. The area of the second surface 52 is 85% or more, and preferably 92%, of the area of the inner major side surface 40.

The second rim 54 is located outward of (as viewed in plan) the first rim 44. The second rim 54 has an inner surface 56, which extends perpendicular to the second surface 52 and extends entirely around the upper plate 20, and a curved outer surface 58. The inner surface 56 of the second rim 54, and the second surface 52, together define a shallow cavity or recess 60 in the outer major side surface 50 of the upper plate 20. The second surface 52 forms the bottom of the recess 60.

The distance by which the second rim 54 projects from the second surface 52 is less than the distance by which the first rim 44 projects from the first surface 42. Thus, the recess 60 in the outer major side surface 50 of the upper plate 20 is shallower than the recess 48 in the inner major side surface 40 of the upper plate.

The second surface 52 of the upper plate 20 is inclined relative to the first surface 42 of the upper plate. The second surface 52 is inclined at an angle in the range of from about 1.5° to about 7.5° relative to the first surface 42. In the illustrated preferred embodiment, the second surface 52 is inclined at an angle of 5° relative to the first surface 42. In another preferred embodiment, not illustrated, the second surface 52 is inclined at an angle of 2.5° relative to the first surface 42.

The first and second surfaces 42 and 52 are oriented relative to each other so that they are closest together at the posterior portion 24 of the upper plate 20, and farthest apart at the anterior portion 22 of the upper plate. The second surface 52 is inclined away from the first surface 42 as the second surface 52 extends from the posterior to the anterior of the disc 10. Thus, the first and second surfaces 42 and 52 diverge as they extend from the posterior portion 24 of the upper plate 20 to the anterior portion 22 of the upper plate. This divergence of the first and second surfaces 42 and 52 gives the upper plate 20 a wedge-shaped configuration as viewed in a lateral or medial direction (FIG. 4).

A single projection in the form of a dome 62 extends from the second surface 52 of the upper plate 20. The dome 62 has a crescent-shaped configuration including a central portion 64 and two opposite tips 66 and 68 (see FIG. 3). The dome 62 is oriented on the second surface 52 so that the tips 66 and 68 of the crescent-shaped configuration point generally posteriorly and the central portion 64 of the crescent-shaped configuration is located anteriorly of the tips. The dome 62 is also located anteriorly of the axis 28.

The dome 62 has a side surface 70. The side surface 70 of the dome includes a generally concave surface 71 which faces posteriorly and a generally convex surface 73 which faces anteriorly. The concave surface 71 and the convex surface 73 terminate at the tips 66 and 68 of the dome 62 to form the crescent-shaped configuration of the dome. The concave surface 71 and the convex surface 73 each extend generally perpendicular to the second surface 52.

A crescent-shaped top surface 72 of the dome extends between and interconnects the concave surface 71 and the convex surface 73 of the dome 62. The top surface 72 of the dome 62 forms a part of the outer major side surface 50 of the upper plate 20. The top surface 72 of the dome 62 and the convex surface 73 define an edge 75 on the anterior side of the spinal disc 10.

The top surface 72 of the dome 62 is inclined at a small angle to the second surface 52. As a result, the part of the top surface 72 which is disposed on the central or anterior portion 64 of the dome 62, is farther from the second surface 52 than are the parts of the top surface which are disposed on the tips 66 and 68 of the dome. The central portion 64 of the dome 62 projects 1.7 millimeters above the second surface 52, while the tips 66 and 68 of the dome project 1.3 millimeters above the second surface. The top surface 72 is inclined at an angle in the range of from about 2° to about 6°, and preferably about 4°, relative to the second surface 52. In the illustrated embodiment, the top surface 72 of the dome 62 is inclined at an angle of 3.8° to the second surface 52 of the upper plate 20, that is, at an angle of 8.8° to the first surface 42.

The outer surface 58 of the second rim 54 merges with an outer peripheral side surface 74 of the upper plate 20. The outer peripheral side surface 74 of the upper plate 20 extends perpendicular to the first surface 42 of the upper plate and also extends entirely around the upper plate. Thus, the outer peripheral side surface 74 of the upper plate 20 is not perpendicular to the plane of the second surface 52. Because of the inclination of the second surface 52 to the first surface 42, the outer peripheral side surface 74 of the upper plate 20 has a greater axial extent in the anterior portion 22 of the upper plate (to the right as viewed in FIG. 5) than in the posterior portion 24 of the upper plate (to the left as viewed in FIG. 5).

The upper plate 20 has an outer peripheral flange 78 which extends around the periphery of the upper plate. The flange 78 has a generally planar first surface 80 which extends outward from the outer peripheral side surface 74, in a direction parallel to the first surface 42. The first surface 80 of the flange 78 forms a part of the outer major side surface 50 of the upper plate 20. The flange 78 has a curved second surface 82 which extends downward (as viewed in FIG. 5) and inward from the first surface 80 of the flange.

A planar third surface 84 of the flange 78 extends inward from the second surface 82, in a direction parallel to the first surface 80 of the flange and parallel to the first surface 42 of the upper plate 20. The third surface 84 of the flange 78 lies in a plane located between the plane of the first surface 42 of the upper plate 20 and the plane of the second surface 52 of the upper plate. The third surface 84 of the flange 78 extends from a location outward of the outer peripheral side surface 74, to a location inward of the outer peripheral side surface 74, and merges with the outer surface 46 of the first rim 44. The second and third surfaces 82 and 84 of the flange 78 form a part of the inner major side surface 40 of the upper plate 20.

A porous coating 90 (FIGS. 4 and 6) is located in the recess 48 in the inner major side surface 40 of the upper plate 20. The coating 90 is formed on the first surface 42 and is circumscribed by, or lies inward of, the first rim 44. The coating 90 covers the entire extent of the first surface 42. The coating 90 comprises a layer of small spherical particles or beads 92.

The beads 92 are preferably made of commercially pure titanium, but could be made of any suitable biocompatible material. The beads 92 are sized such that none of the beads pass through a 25 mesh U.S. Series Sieve and all the beads pass through a 40 mesh U.S. Series Sieve. The beads 92 are preferably adhered to the upper plate 20 by diffusion bonding. The beads 92 can, alternatively, be applied to the upper plate 20 by any other suitable technique.

The coating 90 of beads 92 is firmly adhered to the upper plate 20 and is incapable of removal by normal abrasions. As described below, the coating 90 in combination with a primary adhesive interlocks with the material of the elastomeric core 200 to provide a strong bond between the upper plate 20 and the elastomeric core 16. The coating 90 of beads 92 does not project past the first rim 44, that is, in a downward direction as viewed in FIG. 4 and.6.

A porous coating 94 (FIGS. 2, 4 and 6) is located in the recess 60 in the outer major side surface 50 of the upper plate 20. The coating 94 is made from beads 96 which are the same size as, and are applied in the same manner as, the beads 92 on the first surface 42. The coating 94 is formed on the second surface 52 of the upper plate 20 and is circumscribed by, or lies inward of, the second rim 54. The coating 94 covers the entire extent of the second surface 52. The coating 94 also covers the dome 62.

The coating 94 on the second surface 52, as described below, provides for ingrowth of bony tissue when the disc 10 is implanted in the spine 16. The coating 94 of beads 96 is thicker than the depth of the recess 60. Thus, the beads 96 of the coating 94 project axially outward past the second rim 54. This is in contrast to the coating 90, which does not project axially outward past the first rim 44.

The lower plate 120 is identical in configuration to the upper plate. The lower plate 120 is rigid and is made from the same material as the upper plate. The lower plate 120 (FIG. 5) has an anterior portion 122 which is disposed anteriorly in the spine 16 when the disc 10 is implanted in the spine. A posterior portion 124 of the lower plate 120 is disposed posteriorly in the spine 16 when the disc 10 is implanted in the spine.

The configuration of the lower plate 120 as viewed in plan (FIG. 3) is the same as the configuration of the upper plate 20. The perimeter of the lower plate 120 has a flat posterior portion and a curved convex portion which extends between opposite ends and of the flat portion of the perimeter. The lower plate 120, like the upper plate 20, does not have any outwardly projecting lobes.

The lower plate 120 has an inner major side surface 140 (FIG. 5) which is presented upward as viewed in FIG. 5. The inner major side surface 140 includes all of the surface area of the lower plate 120 which is visible from above (in plan) as viewed in FIG. 5. The inner major side surface 140 of the lower plate 120 includes a planar third surface 142 of the lower plate 120 which extends perpendicular to the axis 28. The area of the first surface 142 is at least 65% or more of the area of the inner major side surface 140 as viewed in plan, that is, with all points on the inner major side surface 140 viewed in a direction parallel to the axis 28. Preferably, the area of the third surface 142 is 75% of the area of the inner major side surface 140.

The third surface 142 is circumscribed by a first rim 144 of the lower plate 20. The first rim 144 has a generally semi-cylindrical cross-sectional configuration as shown in FIG. 5 including an arcuate outer surface 146. The outer surface 146 on the first rim 144, and the third surface 142, together define a shallow cavity or recess 148 in the inner major side surface 140 of the lower plate 120. The third surface 142 forms the bottom of the recess 148. The outer surface 146 on the first rim 144 forms a part of the inner major side surface 140 of the lower plate 120.

The lower plate 120 has an outer major side surface 150 which is presented downward as viewed in FIG. 5. The outer major side surface 150 includes all of the surface area of the lower plate 120 which is visible from below (in plan) as viewed in FIG. 5.

The outer major side surface 150 of the lower plate 120 includes a planar fourth surface 152 of the lower plate. The fourth surface 152 is circumscribed by a second rim 154 of the lower plate 120. The area of the fourth surface 152 is greater than the area of the third surface 142. The area of the fourth surface 152 is 85% or more, and preferably 92%, of the area of the inner major side surface 140.

The second rim 154 is located outward of (as viewed in plan) the first rim 144. The second rim 154 has an inner surface 156, which extends perpendicular to the second surface 152 and extends entirely around the lower plate 120, and a curved outer surface 158. The inner surface 156 of the second rim 154, and the fourth surface 152, together define a shallow cavity or recess 160 in the outer major side surface 150 of the lower plate 120. The fourth surface 152 forms the bottom of the recess 160.

The distance by which the second rim 154 projects from the fourth surface 152 is less than the distance by which the first rim 144 projects from the third surface 142. Thus, the recess 160 in the outer major side surface 150 of the lower plate 120 is shallower than the recess 148 in the inner major side surface 140 of the lower plate.

The fourth surface 152 of the lower plate 120 is inclined relative to the third surface 142 of the lower plate. The fourth surface 152 is inclined at an angle in the range of from about 1.5° to about 7.5° relative to the third surface 142. In the illustrated preferred embodiment, the fourth surface 152 is inclined at an angle of 5° relative to the third surface 142. In another preferred embodiment, not illustrated, the fourth surface 152 is inclined at an angle of 2.5° relative to the third surface 142.

The third and fourth surfaces 142 and 152 are oriented relative to each other so that they are closest together at the posterior portion 124 of the lower plate 120, and farthest apart at the anterior portion 122 of the lower plate. The fourth surface 152 is inclined away from the third surface 142 as the fourth surface 152 extends from the posterior to the anterior of the disc 10. Thus, the third and fourth surfaces 142 and 152 diverge as they extend from the posterior portion 124 of the lower plate 120 to the anterior portion 122 of the lower plate. This divergence of the third and fourth surfaces 142 and 152 gives the lower plate 120 the same wedge-shaped configuration as the upper plate 20.

A single projection in the form of a dome 162 extends from the fourth surface 152 of the lower plate 120. The dome 162 has a crescent-shaped configuration including a central portion 164 and two opposite tips 166 and 168 (see FIG. 3). The dome 162 is oriented on the fourth surface 152 s0 that the tips 166 and 168 of the crescent-shaped configuration point generally posteriorly and the central portion 164 of the crescent-shaped configuration is located anteriorly of the tips. The dome 162 is also located anteriorly of the axis 28.

The dome 162 has a side surface 170. The side surface 170 of the dome includes a generally concave surface 171 which faces posteriorly and a generally convex surface 173 which faces anteriorly. The concave surface 171 and the convex surface 173 terminate at the tips 166 and 168 of the dome 162 to form the crescent-shaped configuration of the dome. The concave surface 171 and the convex surface 173 each extend generally perpendicular to the fourth surface 152.

A crescent-shaped top surface 172 of the dome extends between and interconnects the concave surface 171 and the convex surface 173 of the dome 162. The top surface 172 of the dome 162 forms a part of the outer major side surface 150 of the lower plate 120. The top surface 172 of the dome 162 and the convex surface 173 define an edge 175 on the anterior side of the spinal disc 10.

The top surface 172 of the dome 162 is inclined at a small angle to the fourth surface 152. As a result, the part of the top surface 172 which is disposed on the central or anterior portion 164 of the dome 162, is farther from the fourth surface 152 than are the parts of the top surface which are disposed on the tips 166 and 168 of the dome. The central portion 164 of the dome 162 projects 1.7 millimeters above the fourth surface 152, while the tips 166 and 168 of the dome project 1.3 millimeters above the fourth surface. The top surface 172 is inclined at an angle in the range of from about 2° to about 6°, and preferably about 4°, relative to the fourth surface 152. In the illustrated embodiment, the top surface 172 of the dome 162 is inclined at an angle of 3.8° to the fourth surface 152 of the lower plate 120, that is, at an angle of 8.8° to the third surface 142.

The outer surface 158 of the second rim 154 merges with an outer peripheral side surface 174 of the lower plate 120. The outer peripheral side surface 174 extends perpendicular to the third surface 142 of the lower plate 129 and also extends entirely around the lower plate. Thus, the outer peripheral side surface 174 of the lower plate 120 is not perpendicular to the plane of the fourth surface 152. Because of the inclination of the fourth surface 152 to the third surface 142, the outer peripheral side surface 174 of the lower plate 120 has a greater axial extent in the anterior portion 122 of the lower plate (to the right as viewed in FIG. 5) than in the posterior portion 124 of the lower plate (to the left as viewed in FIG. 5).

The lower plate 120 has an outer peripheral flange 178 which extends around the periphery of the lower plate. The flange 178 has a generally planar first surface 180 which extends outward from the outer peripheral side surface 174, in a direction parallel to the third surface 142. The first surface 180 on the flange 178 forms a part of the outer major side surface 150 of the lower plate 120. The flange 178 has a curved second surface 182 which extends upward (as viewed in FIG. 5) and inward from the first surface 180 of the flange.

A planar third surface 184 of the flange 178 extends inward from the second surface 182, in a direction parallel to the first surface 180 of the flange and parallel to the third surface 142 of the lower plate 120. The third surface 184 of the flange 178 lies in a plane located between the plane of the third surface 142 of the lower plate 120 and the plane of the fourth surface 152 of the lower plate. The third surface 184 of the flange 178 extends from a location outward of the outer peripheral side surface 174, to a location inward of the outer peripheral side surface 174, and merges with the outer surface 146 of the first rim 144. The second and third surfaces 182 and 84 of the flange 178 form a part of the inner major side surface 140 of the lower plate 120.

A porous coating 190 (FIG. 4) is located in the recess 148 in the inner major side surface 140 of the lower plate 120. The coating 190 is formed on the third surface 142 and is circumscribed by, or lies inward of, the first rim 144. The coating 190 covers the entire extent of the third surface 142. The coating 190 comprises a layer of small spherical particles or beads 192.

The beads 192 are made from the same material as the beads 92 of the coating 90. The beads 192 are preferably adhered to the lower plate 120 by diffusion bonding. The beads 192 can, alternatively, be applied to the lower plate 120 by any other suitable technique.

The coating 190 of beads 192 is firmly adhered to the lower plate 120 and is incapable of removal by normal abrasions. As described below, the coating 190 in combination with a primary adhesive interlocks with the material of the elastomeric core 200 to provide a strong bond between the lower plate 120 and the elastomeric core 16. The coating 190 of beads 192 does not project axially outward of the first rim 144.

A similar porous coating 194 (FIGS. 3 and 4) is located in the recess 60 in the outer major side surface 150 of the lower plate 120. The coating 194 is formed on the fourth surface 152 and is circumscribed by, or lies inward of, the second rim 154. The coating 194 covers the entire extent of the fourth surface 152. The coating 194 also covers the dome 162. The coating 194 is made from a plurality of beads 196 which are the same as, and are applied in the same manner as, the beads 192 on the third surface 142.

The coating 194 on the fourth surface 152, as described below, provides for ingrowth of bony tissue when the disc 10 is implanted in the spine 16. The layer 190 of beads 196 is thicker than the depth of the recess 160. Thus, the beads 196 of the coating 194 project axially outward past the second rim 154. This is in contrast to the coating 190, which does not project axially outward past the first rim 144.

The elastomeric core 200 is preferably made of a polyolefin rubber or carbon black reinforced polyolefin rubber. The hardness of the elastomeric core is 56–72 shore A durometer. The ultimate tensile strength of the core is greater than 1600 psi. The core has an ultimate elongation greater than 300% using the ASTM D412-87 testing method, and a tear resistance greater than 100 ppi using the ASTM D624-86 testing method. Although the elastomeric core 200 is disclosed as being made of a polyolefin rubber, it can be made of any elastomeric material that simulates the characteristics of a natural disc.

To construct the spinal disc 10, the plates 20 and 120, with the coatings 90, 94, 190 and 194 in place, are cleaned in a methyl ethyl ketone or similar reagent bath for approximately 25 minutes. The plates 20 and 120 are etched, for example with a nitric hydrofluoric acid solution, to remove any oxide coating from the plates. Thereafter, the plates 20 and 120 are rinsed in distilled water, and a primer is applied to the plates that will be bonded to the core 200. The primer is applied within about 2 hours of the etch, and at a nominal thickness of 0.35 mils. After the primer has dried for not less than 60 minutes, an adhesive is applied at a nominal thickness of 0.65 mils. The plates 20 and 120 are then placed in a mold and the elastomeric material of the core 200 is flowed into the mold and adhered to the plates. The elastomeric material of the core 200 is then cured to form the completed disc 10.

The elastomeric core 200, as thus formed, is affixed to the inner major side surface 40 of the upper plate 20. The core 200 has a planar upper surface 202 (FIGS. 2, 4 and 6) which is affixed to and overlies the first surface 42 of the upper plate 20. A portion 204 of the material of the core 200 extends into and interlocks with the first surface 42 of the upper plate 20, as well as with the porous coating 90 on the first surface. The first surface 42 of the upper plate 20 is bonded to the upper surface 202 of the elastomeric core 200 and to the beads throughout the entire extent of the first surface.

Another portion 206 (FIG. 6) of the material of the core 200 extends over and is adhered to the first rim 44 on the upper plate 20. Another portion 208 of the material of the core 200 extends over and is adhered to the planar third surface 84 of the flange 78 of the upper plate 20. Yet another portion 210 of the material of the core 200 extends over and is adhered to the curved second surface 82 of the flange 78 of the upper plate 20. The material portion 210 which overlies the second surface 82 of the flange 78 tapers to a zero thickness, as it approaches the first surface 80 of the flange.

The material of the core 200, as thus formed, is also affixed to the inner side surface 140 of the lower plate 120. A portion of the material of the core 200 extends into and interlocks with the third surface 142 of the lower plate 120, as well as with the porous coating 190 on the third surface. The core 200 has a planar lower surface 212 (FIG. 4) which is affixed to the third surface 142 of the lower plate 120. The lower surface 212 of the core 200 is parallel to the upper surface 202 of the core. The third surface 142 of the lower plate 120 is bonded to the lower surface 212 of the elastomeric core 200 throughout the entire extent of the third surface.

A portion 216 (FIG. 4) of the material of the core 200 extends over and is adhered to the first rim 144 on the lower plate 120. Another portion 218 of the material of the core 200 extends over and is adhered to the planar third surface 184 of the flange 178 of the lower plate 120. Yet another portion 220 of the material of the core 200 extends over and is adhered to the curved second surface 182 of the flange 178 of the lower plate 120. The material portion 220 which overlies the second surface 182 of the flange 178 tapers to a zero thickness, as it approaches the first surface 180 of the flange.

The core 200 has an exposed outer side surface 230 (FIGS. 2, 4 and 6) which extends between the upper and lower plates 20 and 120. The outer side surface 230 of the core 200 includes a first surface portion 232 (FIGS. 4 and 6) extending substantially perpendicular to the first surface 42 of the upper plate 20. The first surface portion 232 is located outward of the flange 78 of the upper plate 20.

A convex second portion 234 of the outer side surface 230 of the core 200 extends from the first surface portion 232, in a direction toward the lower plate 120. A concave third portion 236 of the outer side surface 230 of the core 200 extends from the second surface portion 234, in a direction toward the lower plate 120.

The outer side surface 230 of the core 200 includes a fourth surface portion 238 extending from the third surface portion 236, in a direction substantially perpendicular to the first surface 42 of the upper plate 20 and parallel to the axis 28 of the disc 10. The fourth surface portion 238 is disposed axially at a location between the upper plate 20 and the lower plate 120. The fourth surface portion 238 is disposed inward of the outer periphery of the plate flanges 78 and 178, but outward of the first rims 44 and 144 of the plates.

The fourth surface portion 238 merges with a concave fifth surface portion 240 which is a mirror image of the third surface portion 236. The fifth surface portion 240 merges with a convex sixth surface portion 242 which is a mirror image of the second surface portion 234.

The sixth surface portion 242 merges with a seventh surface portion 244 which is a mirror image of the first surface portion 232. The seventh surface portion 244 is located outward of the flange 178 of the lower plate 120.

The central portion of the core 200, i.e. the portion of the core 200 located between the surface 42 and the surface 142, is of substantially uniform thickness. Because the central portion of the core 200 is of uniform thickness and the plates 20 and 120 are wedge-shaped, the overall configuration of the disc 10 is wedge-shaped. The disc 10 is thicker in the anterior portion 22 of the disc and is thinner in the posterior portion 24 of the disc.

When the disc 10 is in use in the spinal column 16, the upper plate 20 is affixed to the upper vertebra 12. The dome 62 on the upper plate 20 is fitted into a corresponding single recess or cavity 260 (indicated schematically in FIG. 4) formed in the upper vertebra 12. The engagement of the dome 62 of the upper plate 20 in the cavity 260 in the upper vertebra 12 resists relative movement between the upper plate and the upper vertebra.

In the spinal disc 10 of the present invention, the dome 62 has a maximum height from the second surface 52 of about 1.7 mm. In comparison, the spinal disc of U.S. Pat. No. 5,017,437 includes a plurality of cylindrical pegs which project about 2.6 mm from the upper and lower surfaces of the spinal disc for affixation to the vertebrae. As a result, less distraction of the two vertebrae 12 and 14 is needed to place the spinal disc 10 in the spinal column 16, than is needed to place the spinal disc of U.S. Pat. No. 5,017,437.

The configuration of the dome 62 also reduces the tendency for expulsion of the spinal disc 10 from the spinal column 16. Specifically, the convex anterior surface 73 of the dome 62 provides a relatively large vertebral contact area, as viewed in an anterior elevation (from the left as viewed in FIGS. 3 and 5), which contact area extends over about half the width of the spinal disc 10. The concave posterior surface 71 of the dome 62 provides a relatively large vertebral contact area, as viewed in a posterior elevation (from the right as viewed in FIGS. 3 and 5), which contact area extends over about half the width of the spinal disc 10. In addition, the anterior edge 75 on the dome 62, digs into the vertebra to resist expulsion of the spinal disc.

If the spinal disc 10 needs to be removed from the spinal column, the tips 66 and 68 of the dome 62 act as hooks for cooperating with a removal tool (not shown) to enable removal of the spinal disc in an anterior direction.

The crescent-shaped configuration of the dome 62 better enables proper positioning of the spinal disc 10 between vertebrae, as compared to a prior art spinal disc having cylindrical pegs. The surgeon can make one relatively large cavity 260 for receiving the dome 62, as compared to a plurality of small cavities for receiving the cylindrical pegs. This one large cavity makes it easier for the surgeon to adjust the position of the spinal disc 10 between vertebrae, as compared to a spinal disc which has a plurality of smaller projections.

The porous coating 94 on the second surface 52 of the upper plate 20 promotes bone ingrowth between the upper vertebra 12 and the upper plate 20. The second surface 52 (FIG. 6) of the upper plate 20 engages the bony material of the upper vertebra 12. Interlocking engagement between the upper plate 20 and the bony material of the upper vertebra 12 is enhanced by the fact that the beads 96 of the coating 94 project axially outward past the second rim 54.

The lower plate 120 is affixed to the lower vertebra 14. The dome 162 on the lower plate 120 is fitted into a corresponding single recess or cavity 262 (indicated schematically in FIG. 4) formed in the lower vertebra 14. The engagement of the dome 162 of the lower plate 120 in the cavity 262 in the lower vertebra 14 resists relative movement between the lower plate and the lower vertebra. The configuration of the dome 162 on the lower plate 120 has the same advantages as described above with reference to the dome 62 on the upper plate 20.

The porous coating 194 on the fourth surface 152 promotes bone ingrowth between the lower vertebra 14 and the lower plate 120. The fourth surface 152 of the lower plate 120 engages the material of the lower vertebra 14. Interlocking engagement between the lower plate 120 and the bony material of the lower vertebra 14 is enhanced by the fact that the beads 196 of the coating 194 project axially outward past the second rim 154.

The spinal disc 10 does not have any outwardly projecting lobes on the posterior portion 24 of the disc. Therefore, as compared to a prior art disc having an open space between two lobes, stress is spread over a greater area, thus reducing the forces acting to separate the plates 20 and 120 from the body of elastomeric material 200.

From the above description of the invention, those skilled in the art will perceive improvements, changes and modifications in the invention. Such improvements, changes and modifications within the skill of the art are intended to be covered by the appended claims.

What is claimed is:

1. A spinal disc prosthesis formed to replace a damaged spinal disc positioned to lie between upper and lower vertebras in a spinal column, the prosthesis comprising:

a body including a first opposite surface and a second opposite surface adapted to engage the respective upper and lower vertebras and a single projection extending from the first opposite surface, the projection being generally crescent-shaped, wherein the projection includes (i) a posteriorly facing concave side surface and an anteriorly facing convex side surface both extending upwardly from the first opposite surface, and (ii) a top surface extending between the posteriorly facing concave side surface and the anteriorly facing convex side surface, wherein (i) a posterior edge is defined by the intersection of the top surface and the posteriorly facing concave side surface, and (ii) an anterior edge is defined by the intersection of the top surface and the anteriorly facing concave side surface, and wherein the posterior edge is spaced apart from the anterior edge.

2. The prosthesis of claim 1, wherein the body includes a second projection extending from the second opposite surface.

3. The prosthesis of claim 2, wherein the second projection is generally crescent-shaped.

4. The prosthesis of claim 1, wherein the first opposite surface and the second opposite surface of the body are generally rigid.

5. The prosthesis of claim 4, wherein the opposite surfaces of the body are generally rigid.

6. The prosthesis of claim 1, wherein:

the projection further includes (i) a first convex crescent-tip side surface and a second convex crescent-tip side surface both extending upwardly from the first opposite surface, the first convex crescent-tip side surface is interposed at a first location between the posteriorly facing concave side surface and the anteriorly facing convex side surface, the second convex crescent-tip side surface is interposed at a second location between the posteriorly facing concave side surface and the anteriorly facing convex side surface, and the first location is spaced apart from the second location.

7. The prosthesis of claim 6, wherein:

the first convex crescent-tip side surface, the posteriorly facing concave side surface, the second convex crescent-tip side surface, and the anteriorly facing convex side surface collectively define a continuous circuitous surface.

8. The prosthesis of claim 1, wherein the top surface of the projection is substantially flat.

9. A spinal disc prosthesis for replacing a damaged spinal disc in a spinal column of a human, the prosthesis comprising:

an elastomeric core having a superior surface and an inferior surface;

a superior plate coupled to the superior surface of the core;

an inferior plate coupled to the inferior surface of the core, an inferior surface of the superior plate and a superior surface of the inferior plate being generally parallel relative to one another, and a projection extending from the superior plate, the projection including a side wall having a generally concave surface and a generally convex surface, wherein the projection includes a top surface extending between the surfaces of the side wall, and wherein the top surface is inclined relative to the superior plate.

10. A spinal disc prosthesis for replacing a damaged spinal disc in a spinal column of a human, the prosthesis comprising:

an elastomeric core having superior and inferior surfaces, a superior plate coupled to the superior surface of the core, an inferior plate coupled to the inferior surface of the core, an inferior surface of the superior plate and a superior surface of the inferior plate being generally parallel relative to one another, a projection extending from the superior plate, the projection including a side wall having a generally concave surface and a generally convex surface; and an inferior projection extending from the inferior plate, wherein the inferior projection includes a side wall positioned to lie generally perpendicular to the inferior plate, and wherein the inferior projection includes a top surface inclined relative to the inferior plate.

11. A spinal disc prosthesis for replacing a damaged spinal disc in a spinal column of a human, the prosthesis comprising:

a body including a superior plate and an inferior plate, an inferior surface of the superior plate and a superior surface of the inferior plate being positioned to lie generally parallel to one another, the superior plate and the inferior plate each having a perimeter defined by a generally straight portion and a generally curved portion that interconnects opposite ends of the generally straight portion, and a projection extending from one of the superior plate and the inferior plate, the projection being generally crescent-shaped, wherein the projection includes a side wall and a top surface coupled to the side wall, and wherein the top surface is inclined relative to the superior plate of the body.

12. A spinal disc prosthesis, comprising:

an elastomeric core having a superior surface and an interior surface;

a superior plate coupled to the superior surface of the core;

an inferior plate coupled to the inferior surface of the core; and a projection extending from the superior plate, wherein the projection includes (i) a posteriorly facing concave side surface and the anteriorly facing convex side surface both extending upwardly from the superior plate, and (ii) a top surface extending between the posteriorly facing concave side surface and the anteriorly facing convex side surface, wherein (i) a posterior edge is defined by the intersection of the top surface and the posteriorly facing concave side surface, and (ii) an anterior edge is defined by the intersection of the top surface and the anteriorly facing concave side surface, and wherein the posterior edge is spaced apart from the anterior edge.

13. The prosthesis of claim 12, wherein:

the projection further includes (i) a first convex crescent-tip side surface and a second convex crescent-tip side surface both extending upwardly from the first opposite surface, the first convex crescent-tip side surface is interposed at a first location between the posteriorly facing concave side surface and the anteriorly facing convex side surface, the second convex crescent-tip side surface is interposed at a second location between the posteriorly facing concave side surface and the anteriorly facing convex side surface, and the first location is spaced apart from the second location.

14. The prosthesis of claim 13, wherein:

the first convex crescent-tip side surface, the posteriorly facing concave side surface, the second convex crescent-tip side surface, and the anteriorly facing convex side surface collectively define a continuous circuitous surface.

15. The prosthesis of claim 12, wherein the top surface of the projection is substantially flat.

16. A spinal disc prosthesis for replacing a damaged spinal disc in a spinal column of a human, the prosthesis comprising:

a body including a superior plate and an inferior plate, an inferior surface of the superior plate and a superior surface of the inferior plate being positioned to lie generally parallel to one another, the superior plate and the inferior plate each having a perimeter defined by a generally straight portion and a generally curved portion that interconnects opposite ends of the generally straight portion, and a projection extending from one of the superior plate and the inferior plate, the projection being generally crescent-shaped, wherein the projection extends from the superior plate of the body, wherein the projection includes (i) a posteriorly facing concave side surface and an anteriorly facing convex side surface both which extends upwardly from the superior plate, and (ii) a top surface extending between the posteriorly facing concave side surface and the anteriorly facing convex side surface, wherein (i) a posterior edge is defined by the intersection of the top surface and the posteriorly facing concave side surface, and (ii) an anterior edge is defined by the intersection of the top surface and the anteriorly facing concave side surface, and wherein the posterior edge is spaced apart from the anterior edge.

17. The prosthesis of claim 16, wherein:

the projection further includes (i) a first convex crescent-tip side surface and a second convex crescent-tip side surface both extending upwardly from the first plate, the first convex crescent-tip side surface is interposed at a first location between the posteriorly facing concave side surface and the anteriorly facing convex side surface, the second convex crescent-tip side surface is interposed at a second location between the posteriorly facing concave side surface and the anteriorly facing convex side surface, and the first location is spaced apart from the second location.

18. The prosthesis of claim 17, wherein:

the first convex crescent-tip side surface, the posteriorly facing concave side surface, the second convex crescent-tip side surface, and the anteriorly facing convex side surface collectively define a continuous circuitous surface.

19. The prosthesis of claim 16, wherein the top surface of the projection is substantially flat.

* * * * *